United States Patent
Shapira et al.

(10) Patent No.: US 6,387,956 B1
(45) Date of Patent: May 14, 2002

(54) METHODS OF TREATING OBSESSIVE-COMPULSIVE SPECTRUM DISORDERS

(75) Inventors: Nathan A. Shapira; Toby D. Goldsmith, both of Gainesville, FL (US); Paul E. Keck, Jr., Cincinnati, OH (US)

(73) Assignee: University of Cincinnati, Cincinnati, OH (US)

( * ) Notice: Subject to any disclaimer, the term of this patent is extended or adjusted under 35 U.S.C. 154(b) by 0 days.

(21) Appl. No.: 09/534,778

(22) Filed: Mar. 24, 2000

Related U.S. Application Data (60) Provisional application No. 60/125,907, filed on Mar. 24, 1999.

(51) Int. Cl.$^7$ .................................................. A61K 31/135
(52) U.S. Cl. ........................ 514/646; 514/217; 514/321; 514/647; 514/651; 514/654; 514/657; 424/449
(58) Field of Search ................................ 514/646, 217, 514/321, 647, 651, 658, 657; 424/449

(56) References Cited

U.S. PATENT DOCUMENTS 5,780,479 A * 7/1998 Kim ........................... 514/282

OTHER PUBLICATIONS

Shapira et al., Open–Label Pilot Study of Tramadol Hydrochloride in Treatment–Refractory Obssessive–Compulsive Disorder; Depression and Anxiety 6:170–173 (1997).
Hollander, M.D., Obsessive–Compulsive Disorder: The Hidden Epidemic; J. Clin Psychiatry; 58(suppl. 12):3–6 (1997).
Lee, et al., Tramadol: A Preliminary Review of Its Pharmacodynamic and Pharmacokinetics Properties, and Therapeutic Potential in Acute and Chronic Pain States; Drugs 46 (2): 313–340 (1993).
Dayer, et al., The Pharmacology of Tramadol; Drugs 47 (Suppl. 1): 3–7 (1994).
Goodman, et al., Pharmacotherapy of Obsessive Compulsive Disorder; J Clin Psychiatry 53:4 (suppl.), pp. 29–37 (Apr. 1992).
Domingquez, M.D., Serotonergic Antidepressants and Their Efficacy in Obsessive Compulsive Disorder; J Clin Pyschiatry 53:10 (suppl.), pp. 56–59 (Oct. 1992).
Leckman, M.D., "Just Right" Perceptions Associated With Compulsive Behavior in Tourette's Syndrome; Am J Psychiatry 151:5, pp. 675:680 (May 1994).
McConville, et al., Sequential use of opioid antagoinists and agonists in Tourrette'syndrome; The Lancet, vol. 343:601 (Mar. 5, 1994).
Goodman, M.D., et al., The Yale–Brown Obsessive Compulsive Scale; Arch Gen Psychiatry—vol. 46: 1006–1011 (Nov. 1989).
Abstract No. NR 101, "Tramadol for Treatment–Refractory OCD", Abstracts for 150th Annual Meeting of the American Psychiatric Association, May 17–22, 1997.

* cited by examiner

*Primary Examiner*—Frederick Krass
(74) *Attorney, Agent, or Firm*—Dinsmore & Shohl LLP (57) ABSTRACT

A method of treating an obsessive-compulsive spectrum disorder comprises the step of administering an effective amount of tramadol to an individual.

28 Claims, 8 Drawing Sheets

METHODS OF TREATING OBSESSIVE-COMPULSIVE SPECTRUM DISORDERS

This application claims the benefit of U.S. Provisional Application No. 60/125,907, filed Mar. 28, 1999.

TECHNICAL FIELD

This invention relates to methods of treating obsessive-compulsive spectrum disorders. More particularly, the invention relates to methods of treating obsessive-compulsive spectrum disorders comprising the step of administering an effective amount of tramadol to an individual.

BACKGROUND ART

Although originally believed to be rare, it is now known that obsessive-compulsive disorder (OCD) is common, with estimated life time prevalence rates in the United States ranging from 1.9% to 3.3% (Shapira et al., *Depression and Anxiety* 6; 170–173 (1997).) *The Diagnostic and Statistical Manual of Mental Disorders,* fourth edition, (DSM-IV), includes as its diagnostic criteria for OCD that: the person exhibits either obsessions or compulsions; at some point during the course of the disorder the person has recognized that the obsessions or compulsions are excessive or unreasonable; the obsessions or compulsions caused marked stress, are time-consuming or significantly interfere with the person's normal routine, occupational/academic functioning, or usual social activities or relationships; if another axis I disorder is present, the content of the obsessions or compulsions is not restricted to it; and the disturbance is not due to the direct physiologic effects of a substance or a general medical condition.

The DSM-IV sets four indicia of obsessions. First, the person has recurrent and/or persistent thoughts, impulses or images that are experienced at some time during the disturbance as intrusive and inappropriate and as causing marked anxiety or distress. Second, the thoughts, impulses or images are not simply excessive worries about real-life problems. Third, the person attempts to ignore or suppress such thoughts, impulses or images or to neutralize them through some other thought or action. Fourth, the person recognizes that the obsessional thoughts, impulses, or images are products of his or her own mind and are not imposed from without.

The DSM-IV sets forth two indicia of compulsion. First, the person has repetitive behaviors or mental acts that the person feels driven to perform in response to an obsession or according to rules that must be applied rigidly. Repetitive behaviors include hand washing, ordering and checking, while mental acts include praying, counting and repeating words silently. Second, the behaviors or mental acts are aimed at preventing some dreaded event or situation; however, these behaviors or mental acts either are not connected in a realistic way to what they are designed to neutralize or prevent, or are clearly excessive.

Individuals who meet the DSM-IV criteria for OCD can be scored using the Yale-Brown Obsessive-Compulsive Scale (Y-BOCS). Y-BOCS scores range from 0 to 40. Generally, 0 to 7 is considered a subclinical syndrome, 8–15 is considered mild, 16–23 is considered moderate, 24–31 is considered severe, and 32–40 is considered extremely severe.

A wide range of psychiatric and neuropsychiatric disorders appear to be related to OCD and form a family of related disorders referred to as obsessive-compulsive (OC) spectrum disorders. Obsessive-compulsive spectrum disorders include somatoform disorders, eating disorders, impulse control disorders (ICDs), paraphilia and non-paraphilic sexual addictions, Sydeham's chorea, torticollis, autism, and movement disorders, including Tourette's syndrome. As used herein, "obsessive-compulsive spectrum disorders" is intended to include OCD.

Somatoform disorders include body dysmorphic disorder (BDD) and hyperchondriasis. Body dysmorphic disorder (BDD) is a preoccupation with an imagined slight defect in appearance that causes significant distress or impairment in functioning. Individuals suffering from BDD have preoccupations similar to OCD obsessions in that they have repetitive intrusive thoughts, often perform time-consuming, repetitive and sometimes ritualistic behaviors. Hypochondriasis is a preoccupation with the fear of having, or the idea that one has, a serious disease based on the person's misinterpretation of bodily signs or symptoms. Hypochondriacal preoccupations resemble OCD obsessions in that they are often experienced as intrusive and persistent, and the individuals often display repetitive checking behaviors.

Eating disorders include anorexia nervosa, bulimia nervosa and binge eating disorder (BED). The DSM-IV defines anorexia nervosa as a refusal to maintain a minimally normal body weight; intensive fear of gaining weight or becoming fat even though underweight; significant disturbance in perception of body shape or size; and, in females, amenorrhea. The DSM-IV defines bulimia nervosa as recurrent episodes of binge eating followed by inappropriate compensatory behaviors designed to prevent a weight gain. BED is characterized by recurrent episodes of binge eating in the absence of regular use of inappropriate compensatory behaviors. There is some overlap among anorexia nervosa, bulimia nervosa, and BED. However, all three disorders are characterized by a core preoccupation with food and body weight. Individuals suffering from eating disorders often perform specific rituals, and have an abnormal preoccupation with food and weight.

The DSM-IV defines an impulse control disorder (ICD) as the failure to resist the impulse, drive or temptation to perform some act that is harmful. ICDs include intermitted explosive disorder (IED), compulsive buying or shopping, repetitive self-mutilation (RSM), onychophagia, psychogenic excoriation, kleptomania, pathological gambling, and trichotillomania. Most individuals suffering from ICDs experience increasing sense of tension or arousal before committing the act, then pleasure, gratification or relief at the time of committing the act. Individuals suffering from ICD often experience impulses which are intrusive, persistent and associated with anxiety or tension. Individuals suffering from paraphilias and nonparaphilic sexual addictions (NPSAs) experience similar increasing senses of tension or arousal before committing the act, then pleasure, gratification or relief at the time of committing the act.

Tourette's syndrome is a chronic neuropsychiatric disorder characterized by motor tics and one or more vocal tics beginning before the age of 18 years. The DSM-IV defines a tic as a sudden, rapid, recurrent, nonrhythmic, stereotyped motor movement or vocalization. Tourette's syndrome patients may be able to suppress tics for varying lengths of time, but eventually experience them as irresistible and perform them. Tourette's patients exhibit obsessions resembling OCD obsessions, for example, they often feel the need to perform tics until they are felt to be "just right."

Autism is characterized by difficulties with social interaction, speech and communication, and by a compulsive core. Autistic individuals often display compulsive, repetitive behaviors.

Behavior modification therapy is often efficacious in treating obsessive-compulsive spectrum disorders, including OCD. However, behavior modification therapy generally requires prolonged periods of treatment. Also, an individual may not respond favorably to behavior modification therapy unless the severe OC spectrum disorder symptoms are first controlled or decreased. Thus, it is often desirable to supplement the initial stages of behavior modification with drug therapy. Preferably, the drug therapy will be one that has a short onset of action, preferably less than two weeks.

Some OC spectrum disorders, such a bulimia nervosa, have been shown to respond to monoamine oxidase inhibitors (MAOIs). Unfortunately, people who use MAOIs adhere to numerous dietary restrictions and observe special precautions to avoid drug interactions.

OCD has been treated with serotonin reuptake inhibitors (SRIs) such as clomipramine, fluoxetine, fluvoxamine, sertraline and paroxetine. There is also evidence to suggest that Tourette's syndrome, hypochondriasis, anorexia nervosa, and ICDs such as intermitted explosive disorder (IED), kleptomania, pathological gambling, trichotillomania, compulsive shopping, onychophagia and psychogenic excoriation may respond to SRIs. (Goldsmith et al., *Conceptual Foundations of Obsessive-Compulsive Spectrum Disorder*, in *Obsessive-Compulsive Disorder*, Richard P. Swinson et al. Editors, The Guilford Press. pages 397–425 (1998).) SRIs have also been used to treat compulsive symptoms in autism. (Hollander, *J. Clim. Psychiatry*, 58(12): 3–6 (1997).)

Unfortunately, some individuals are refractory to serotonin reuptake inhibitors. From approximately 30 to 50% of individuals do not respond at all to serotonin reuptake inhibitors, while many who do respond do so only partially. Further, serotonin reuptake inhibitors have a slow onset of action and often require eight to ten weeks of treatment to achieve a significant reduction in symptoms. Also, individuals suffering from movement disorders, such as Tourette's syndrome, often desire a drug that can be taken pro re nata (on an as-needed basis).

Thus there is a need for a therapeutic agent for the treatment of SRI-refractory individuals suffering from obsessive-compulsive spectrum disorders. Further, there is a need for a pharmacological agent which has a short onset of action, preferably less than two weeks. There is an additional need for a drug which can be taken as needed for tic disorders.

Tramadol ((±)cis-2-[(dimethylamino)methyl]-1-(3-methoxyphenyl) cyclohexanol) and its derivatives, including tramadol salts such as tramadol hydrochloride ((±) cis-2-[(dimethylamino)methyl]-1-(3-methoxyphenyl) cyclohexanolhydrochloride), are synthetic analgesic compounds. It is believed tramadol and its salts and other derivatives act through two complimentary mechanisms, one mechanism is binding to mu-opioid receptors and the other mechanism is weak inhibition of norepinephrine and serotonin reuptake. Although physicians are often reluctant to prescribe opioid agonist due to significant abuse potential, tramadol's low abuse liability, low physical dependence and mild tolerance would make it a desirable therapeutic alternative to SRIs for individuals with OC spectrum disorders.

SUMMARY OF THE INVENTION

Accordingly, it is an object of this invention to obviate various problems of the prior art.

It is an object of this invention to provide novel methods for treating obsessive-compulsive spectrum disorders.

It is also an object of this invention to treat obsessive-compulsive spectrum disorders in individuals who are refractory to selective serotonin reuptake inhibitors.

It is an additional object of this invention to provide methods of treating obsessive-compulsive spectrum disorders, which methods provide a rapid onset of response.

It is also an object of this invention to provide a method of treating obsessive-compulsive spectrum disorders, particularly Tourette's syndrome, on an as-needed basis.

In accordance with one aspect of the present invention, methods of treating obsessive-compulsive spectrum disorders comprise administering an effective amount of tramadol, preferably tramadol hydrochloride, to an individual.

In accordance with another aspect of the present invention, methods of obtaining rapid treatment responses for obsessive-compulsive spectrum disorders comprise administering an effective amount of tramadol, preferably tramadol hydrochloride, to an individual.

In accordance with another aspect of the present invention, methods of treating obsessive-compulsive spectrum disorders, particularly Tourette's syndrome, comprise administering an effective amount of tramadol, preferably tramadol hydrochloride, to an individual on an as-needed basis.

It has now been found that tramadol, which is primarily used for analgesia, can provide efficacious treatment of obsessive-compulsive spectrum disorders. Tramadol has been found to provide a rapid response, to be efficacious in serotonin reuptake inhibitor-refractory individuals, and to be useful in an as-needed dosing regime for movement disorders.

These and additional objects and advantages will be more fully apparent in view of the following description.

BRIEF DESCRIPTION OF THE DRAWINGS

While the specification concludes with claims particularly pointing out and distinctly claiming the present invention, it is believed the same will be better understood from the following description taken in conjunction with the accompanying drawings in which:

DETAILED DESCRIPTION

Figure 1:
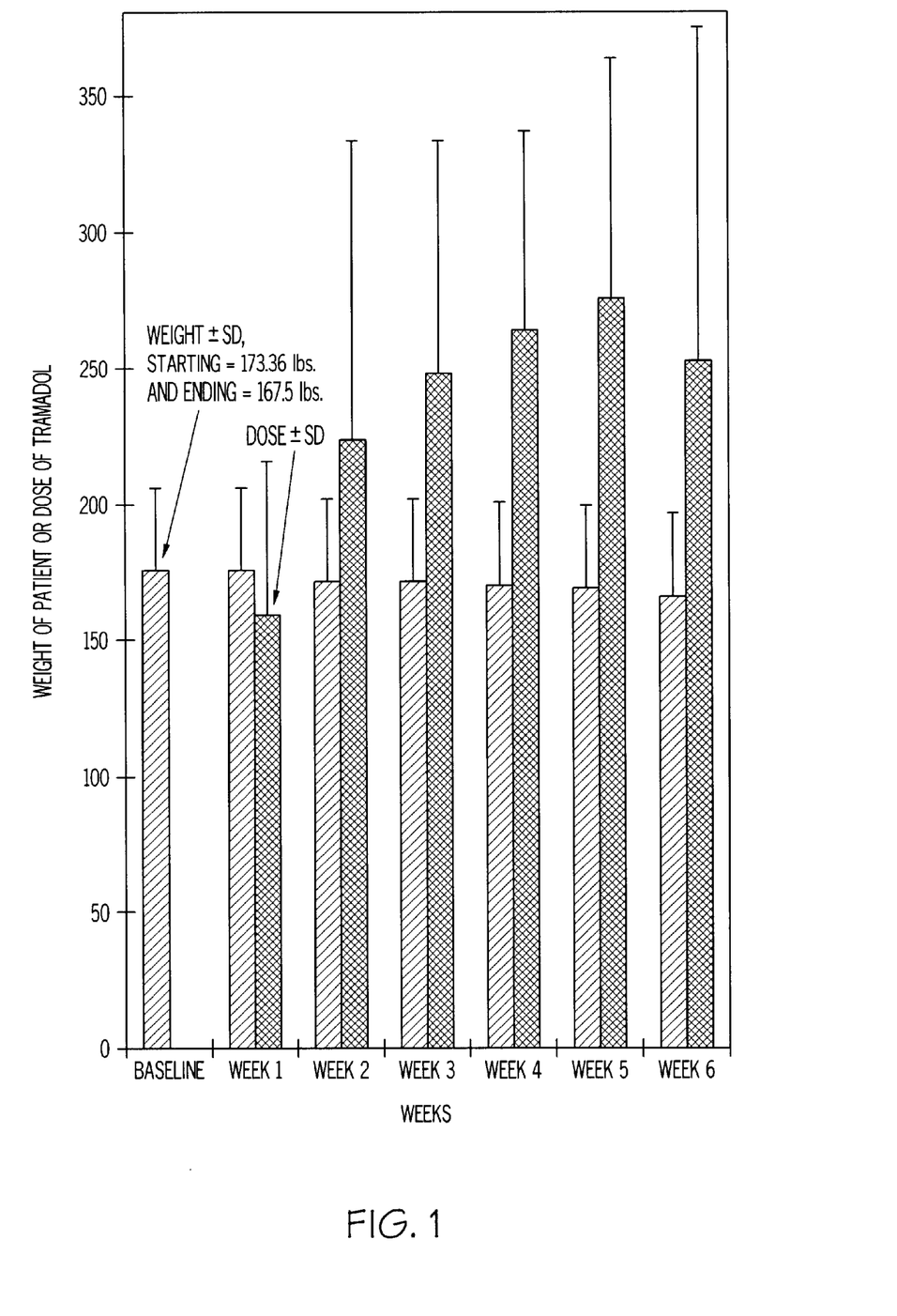
FIG. 1 is a graphical representation of the weekly mean ± standard deviation of weight and tramadol doses for seven patients. The first columns in each of weeks 1–6 represent weight in pounds while the second columns represent total daily tramadol hydrochloride dose in milligrams.
Figure 2:
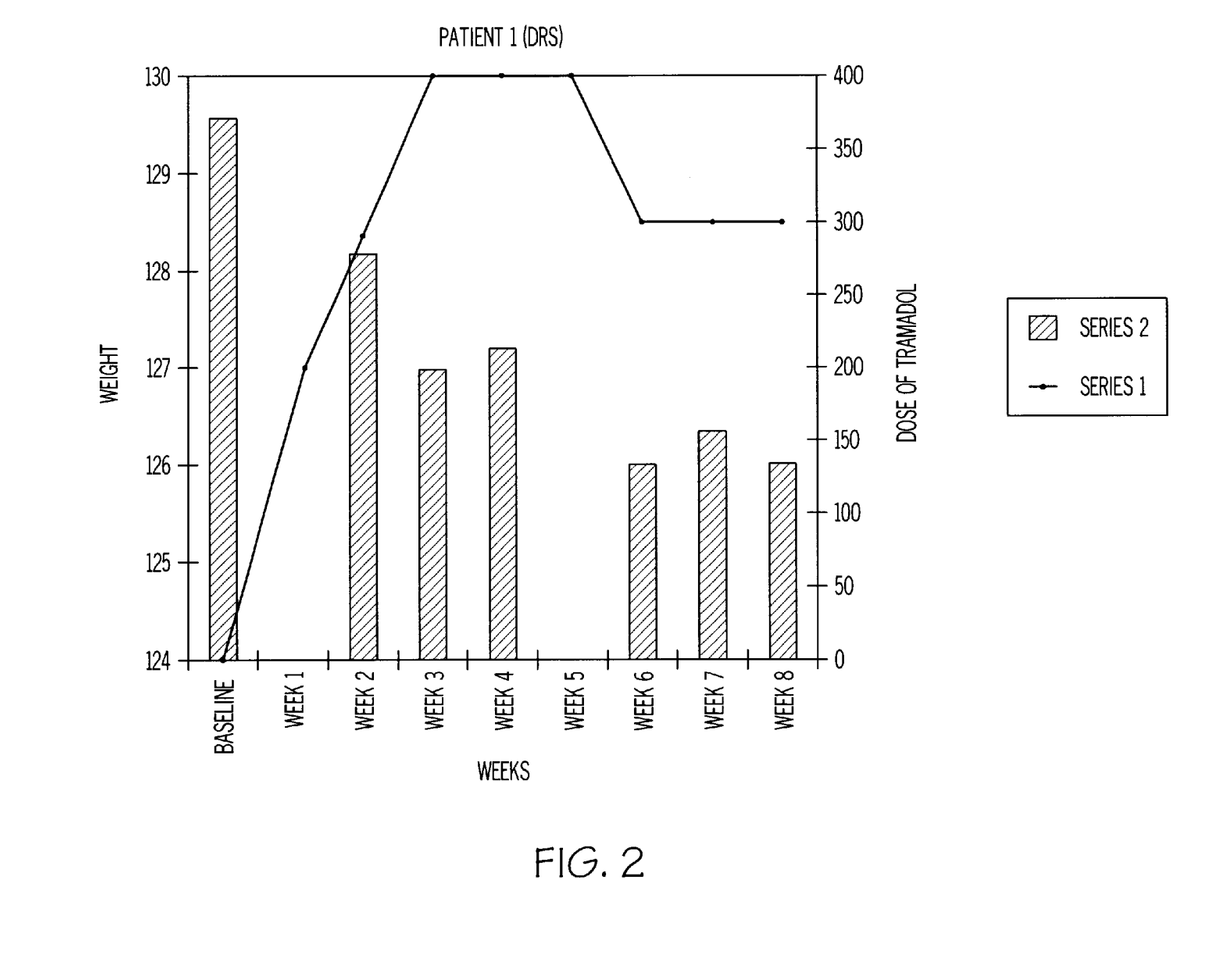
FIGS. 2–8 are graphical representations of the weekly weight and tramadol dose for the individual patients. In each of FIGS. 2–8, Series 1 represents total daily tramadol hydrochloride dose weight while Series 2 refers to weight in pounds.
Figure 3:
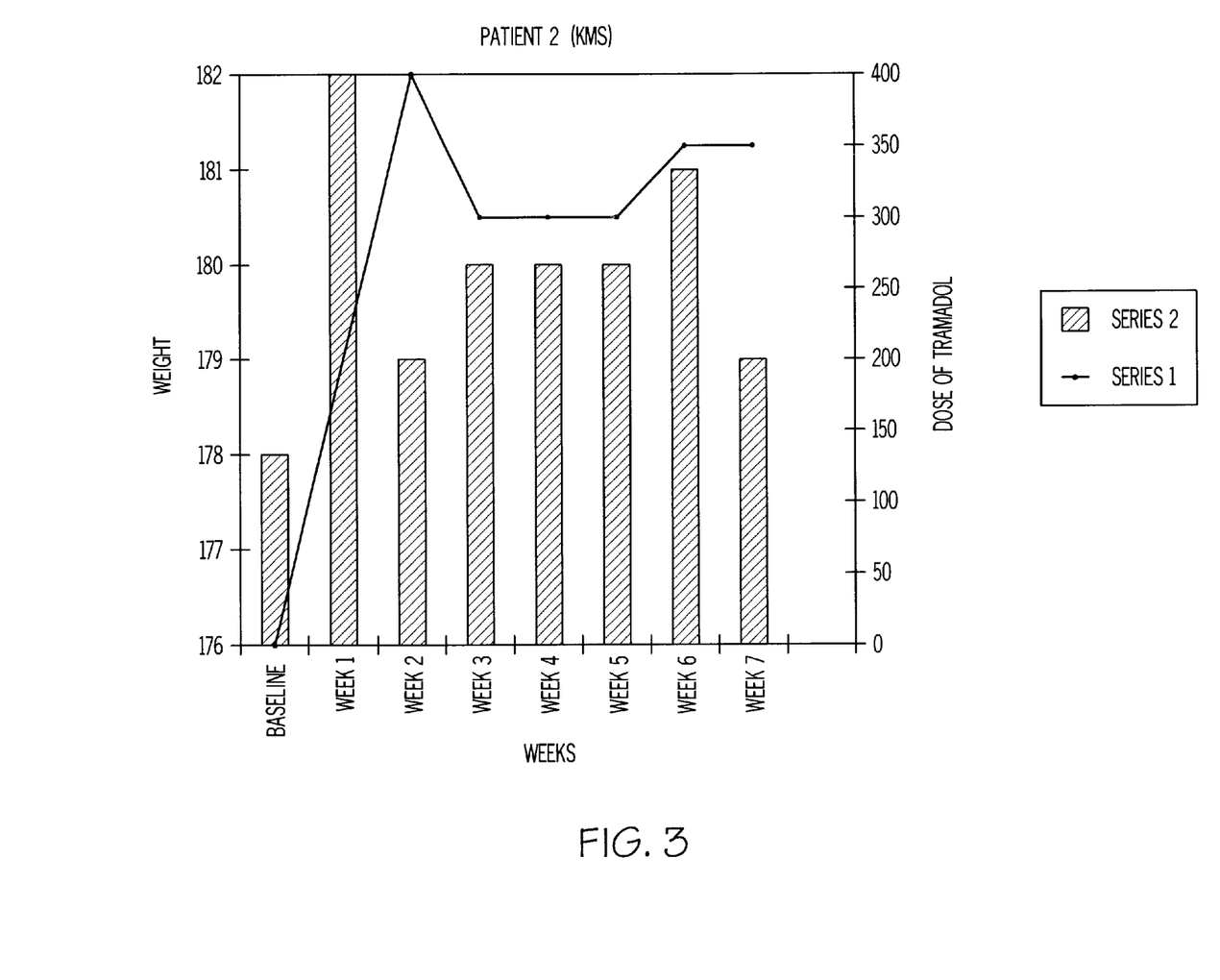
Figure 4:
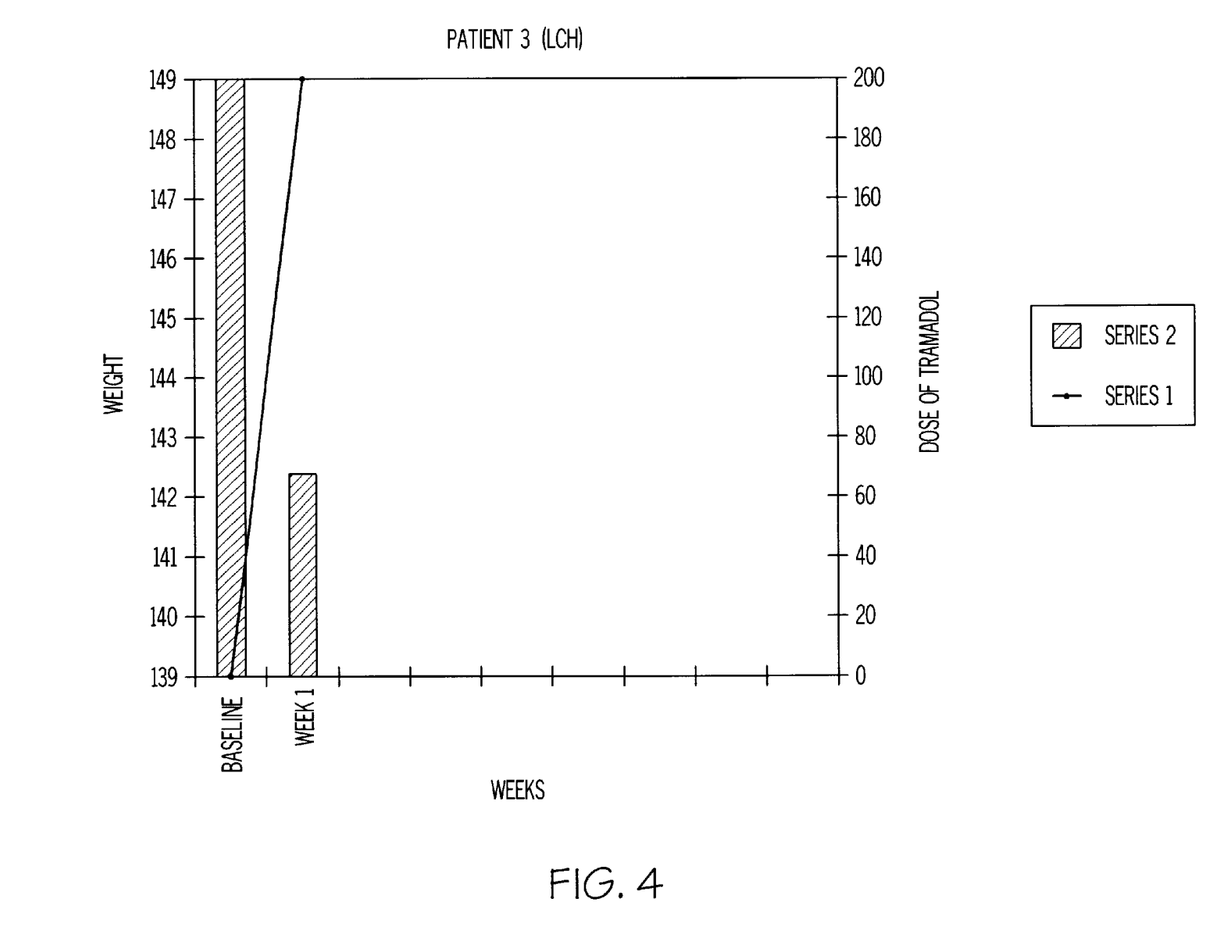
Figure 5:
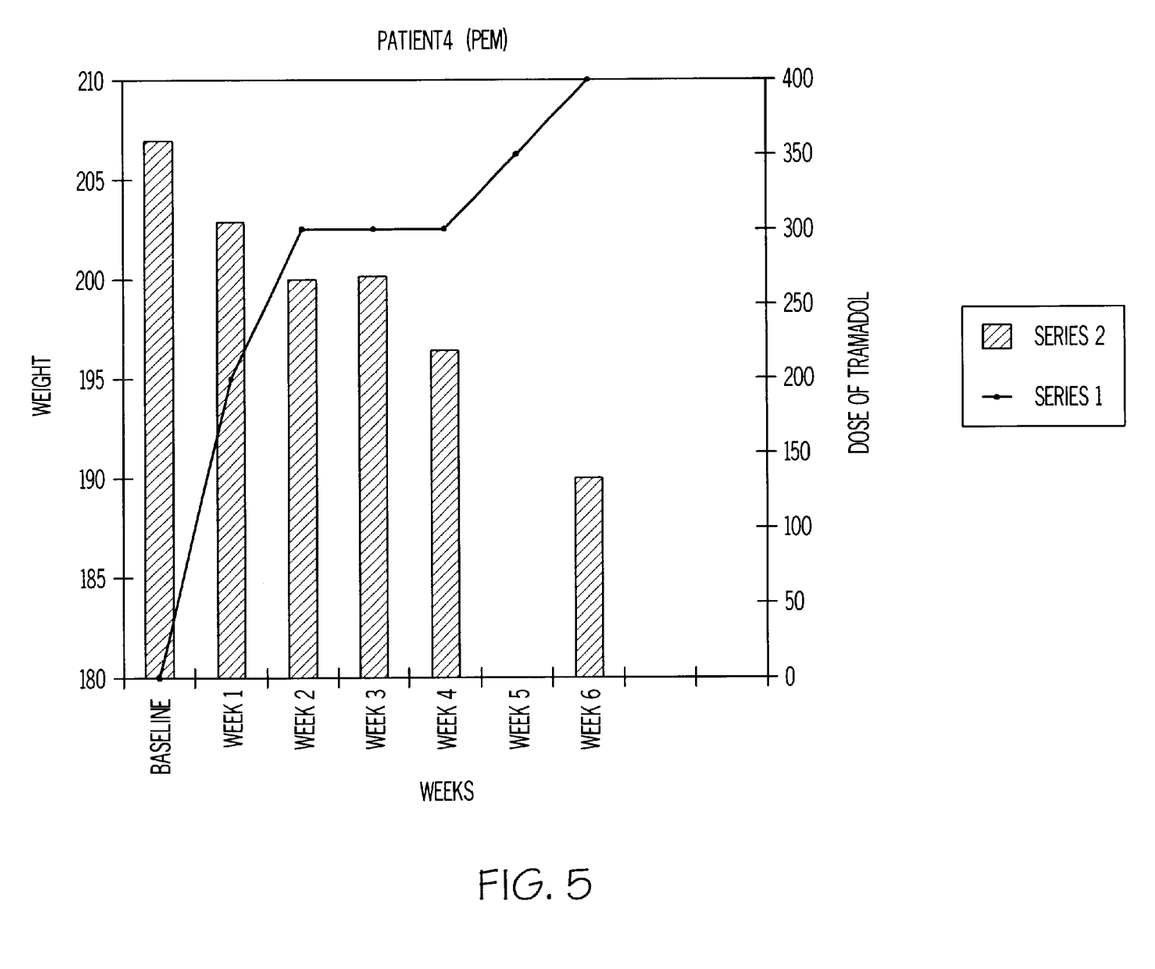
Figure 6:
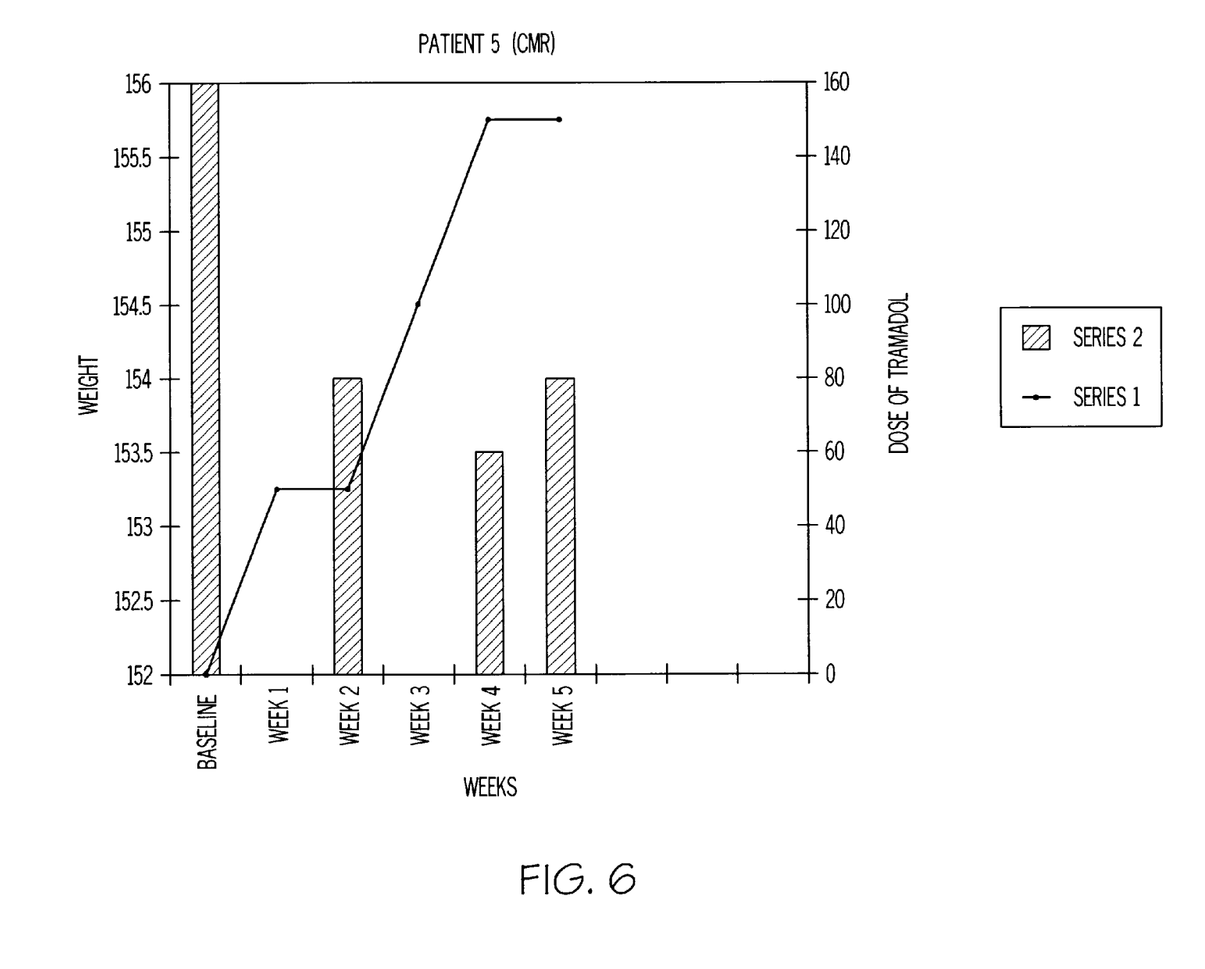
Figure 7:
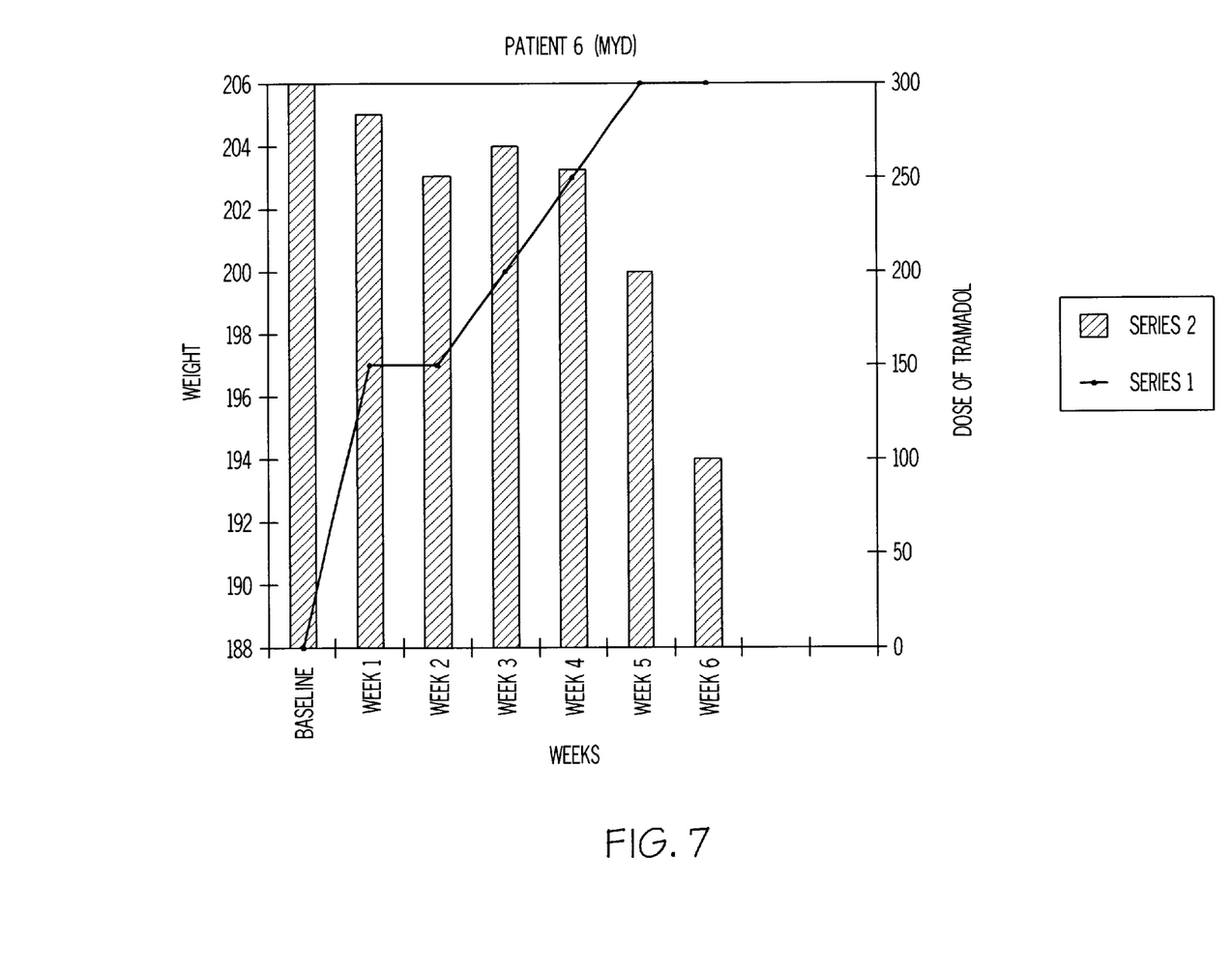
Figure 8:
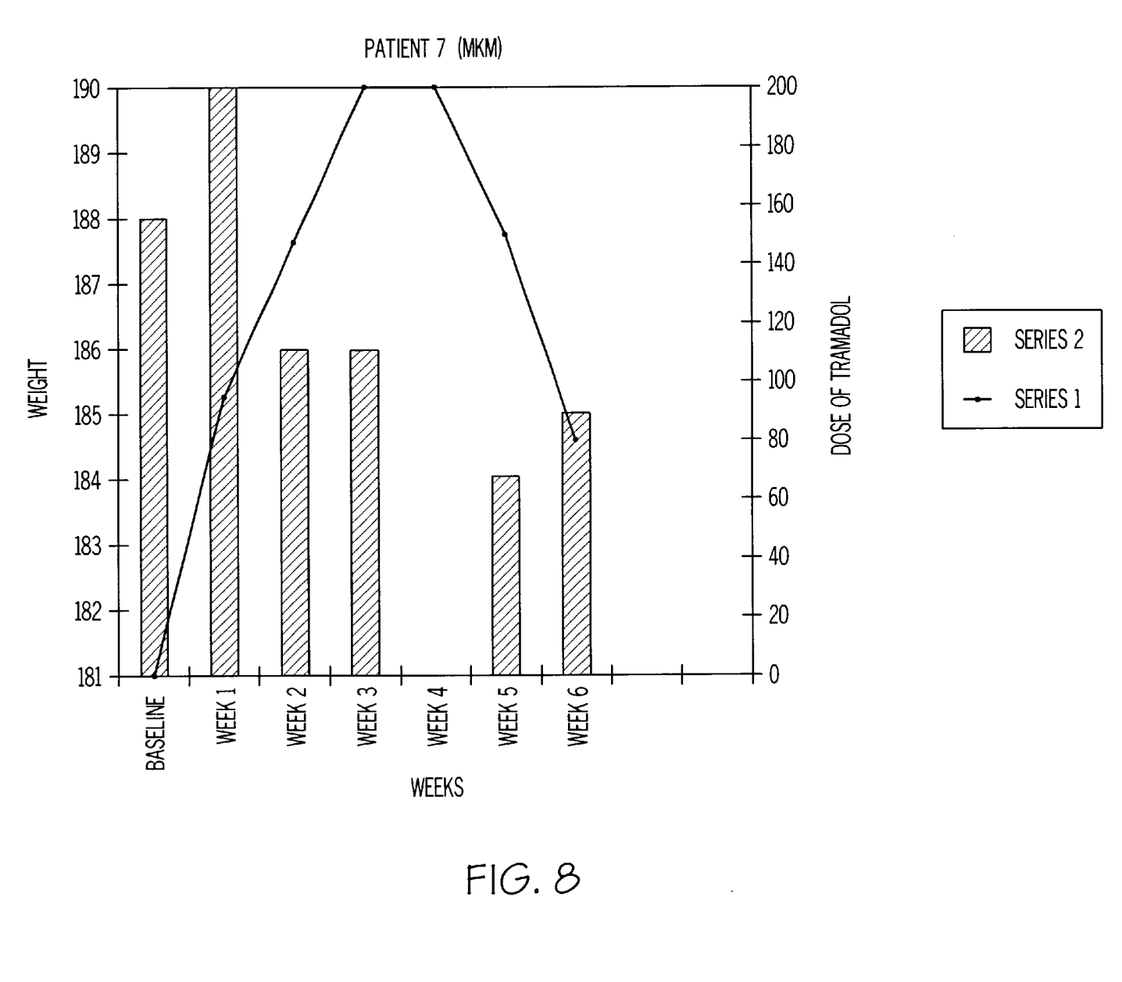

Applicants have found that tramadol, which is primarily used as an analgesic, provides therapeutic benefits for individuals with obsessive-compulsive (OC) spectrum disorders, including obsessive-compulsive disorder. Tramadol has been found to be particularly useful in treating individuals which are refractory to serotonin reuptake inhibitors (SRIs). Applicants have also found a surprisingly rapid onset of response in tramadol-treated individuals as compared to SRI-treated individuals, and have also found that it is possible to treat OC spectrum disorder symptoms on an as-needed basis with tramadol.

As used herein, "obsessive-compulsive spectrum disorders" is intended to include obsessive-compulsive disorder (OCD), somatoform disorders, eating disorders, impulse control disorders, paraphilias and nonparaphilic sexual addictions, Sydeham's chorea, torticollis, autism, and movement disorders. Somatoform disorders include body dysmorphic disorder (BDD) and hypochondriasis; eating disorders include anorexia nervosa, bulimia nervosa and binge-eating disorder (BED); impulse control disorders (ICDs) include intermittent explosive disorder (IED), kleptomania, pathological gambling, pyromania, compulsive buying or shopping, repetitive self-mutilation (RSM), onychophagia, psychogenic excoriation; trichotillomania; and movement disorders include Tourette's syndrome.

As used herein, "serotonin reuptake inhibitors" is intended to refer to drugs other than tramadol which have the capability of inhibiting the reuptake of the neurotransmitter serotonin. Serotonin reuptake inhibitors (SRIs) include clomipramine, and compounds considered to be selective serotonin reuptake inhibitors (SSRIs) such as fluoxetine, fluvoxamine, sertraline, and paroxetine. Clomipramine is a tricyclic antidepressant believed to influence obsessive and compulsive behaviors through its capacity to inhibit the reuptake of serotonin. Unfortunately, tricyclic antidepressants often cause sedation, weight gain, and anticholinergic effects such as increased heart rate, decreased blood pressure upon standing, blurred vision and confusion. Generally SSRIs such as fluoxetine, fluvoxamine, sertraline and paroxetine are preferred as they have fewer adverse side effects.

The severity of the obsessive-compulsive spectrum disorders, and particularly OCD, is evaluated using the Yale-Brown Obsessive-Compulsive Scale (Y-BOCS). The Y-BOCS assigns numerical value to categories such as the amount of time spent on, interference from, distress from, resistance to, and control over obsession and compulsions. Y-BOCS scores range from 0–40, with 0–7 being subclinical, 8–15 being mild, 16–23 being moderate, 24–31 being severe, and 32–40 being extreme severity. Individuals with moderate to extremely severe obsessive-compulsive spectrum disorders generally have symptoms which interfere with their daily activities.

The treatment methods of the present invention comprise administering an effective amount of tramadol to an individual. As used herein, "tramadol" refers to tramadol and its physiologically acceptable derivatives, such as tramadol salts. A preferred form of tramadol is tramadol hydrochloride (($\pm$)cis-2[(dimethylamino)methyl]-1-(3-methoxyphenyl) cyclohexanol hydrochloride), although other salts or physiologically acceptable forms of tramadol may be employed as well. Treatment with tramadol is an effective means of treating individuals who are refractory to selective serotonin reuptake inhibitors. Further, tramadol is found to have had a rapid onset of response. Thus, tramadol is particularly preferred for individuals exhibiting severe and extremely severe forms of OC spectrum disorders.

The tramadol may be administered in any suitable form, including tablets, liquids, timed release capsules, in the form of a candy such as a lollipop, sprinkles which are mixed with soft foods, sublingual dosing, transepidermal patches, subcutaneous sustained release devices, nasal sprays, rectal suppositories and injections. When a sustained release is desired preferred forms are timed capsules, transepidermal patches, and subcutaneous sustained release devices. When a quick response is desired preferred forms are sublingual dosing and injection. For children, geriatric patients, and patients who might have trouble swallowing or compliance problems, preferred forms are candy, sprinkles, rectal suppositories and liquids.

As used herein, "an effective amount" refers to the minimum amount required to decrease the severity of the OC spectrum disorder symptoms. An individual preferably exhibits a decrease in Y-BOCS scores after about 14 days of treatment, more preferably after about 7 days of treatment. Even more preferably, the individual experiences a decrease in compulsive behavior after about 2 days of treatment.

Preferably the tramadol is in the form of a hydrochloride. Generally, the individual is treated with a total of from about 50 to about 400, preferably from about 100 to about 400, mg of tramadol per day. In one embodiment, the tramadol dose may be divided into from about 2 to about 5, preferably from about 2 to about 3, individual doses a day, with each individual dose being from about 50 to about 200, more preferably from about 50 to about 100, mg of tramadol. In one embodiment the individual is treated with from about 50 to about 100 mg of tramadol two to three times a day. Generally two to three individual doses a day are preferred from efficacy, tolerability and compliance aspects, however, more severely affected individuals may require from four to five individual doses a day to control symptoms.

Alternatively, the tramadol may be administered pro re nata (on an as-needed basis). Preferably the tramadol is administered orally or sublingually.

Many individuals suffering from OC spectrum disorders respond favorably to behavior modification therapy. However, with some individuals the OC spectrum disorder symptoms may be so severe that they interfere with the initiation of behavior modification therapy. For example, an individual with extremely severe OCD directed toward contamination may be reluctant to leave his domicile in order to obtain behavior modification therapy. Such an individual would benefit from a drug therapy which was able to quickly control or decrease the severity of the OCD symptoms, thereby rendering the individual more willing to obtain behavior modification therapy. The rapid onset of response to tramadol allows for an individual's OC spectrum disorder symptoms would provide such a benefit. The tramadol treatment may be initiated prior to or along with the initiation of behavior modification therapy. Individuals who have already initiated behavior modification therapy may also be treated with tramadol. This may be particularly beneficial if it appears the severity of the OC spectrum disorder symptoms is interfering with the behavior modification therapy.

In one preferred embodiment, the individual suffering from an OC spectrum disorder is treated with tramadol during or prior to initiation of behavior modification therapy. Preferably, the tramadol therapy is initiated prior to the initiation of the behavior modification therapy, more preferably at least about 2 days prior to the initiation of the behavior modification therapy, even more preferably at least about 7 days prior to the initiation of the behavior modification therapy. Suitable forms of behavior modification therapy are known in the art, and include exposure and response prevention, thought stopping, saturation therapy, stimulus control therapy, or modeling therapy.

Another surprising advantage of the rapid onset of response of tramadol is the treatment of the symptoms of OC spectrum disorders, particularly Tourette's syndrome, on an as-needed basis. As used herein, "as-needed basis" is intended to refer to a dosing regime wherein the individual takes a pharmacological agent at a time and at a level sufficient to control symptoms as desired. Although tramadol may be prescribed according to a schedule, such as, for example, 100 mg 4 times a day, there may be occasions when an as-needed basis is preferred.

For example, an individual with an OC spectrum disorder may desire to control or decrease symptoms for specific events or occasions. A Tourette's syndrome patient may wish to take tramadol prior to an event such as taking a class or giving a speech, while a bulimia nervosa or BED patient may wish to take tramadol before meals or particular situations which usually lead to binge eating or purging. An individual with compulsive buying may take tramadol before going near stores while an individual with pathologic gambling may take tramadol before exposures to triggers that lead to gambling. OCD patients may wish to take an as-needed dose of tramadol before exposure to a stress-inducing situation. For example, a patient with contamination obsessions and/or cleaning compulsions may take tramadol prior to cleaning a bathroom, while a patient with obsessions of harm may take tramadol prior to caring for children.

Oral administration of an effective dose of tramadol, preferably tramadol hydrochloride, at least about one hour prior to the point in time at which the decrease of symptoms is desired will result in an effective decrease in symptoms. The tramadol will decrease the symptoms for a period of up to about six hours. Generally, the as-needed dose will be from about 50 to about 400 mg of oral tramadol, preferably tramadol hydrochloride.

Tramadol offers an additional benefit for treatment of impulse control disorders involving eating, particularly of bulimia nervosa or BED. It has now been found that tramadol treatment may result in appetite loss. Thus, individuals treated for bulimia nervosa or BED would benefit not only by the control of the obsessive and compulsive symptoms of the disorder, but also by the decrease in appetite and the resulting weight loss which is likely to occur. Thus, in one embodiment an individual suffering from bulimia nervosa or BED is treated with tramadol, preferably tramadol hydrochloride, at a total daily dose of from about 50 to about 400, preferably from about 100 to about 400, mg. The individual generally experiences a decreased appetite after about 14, preferably after about 7, days of treatment.

If desired, the tramadol treatment may be supplemented with a SRI, provided the individual responds at least partially to SRIs. Preferably the SRI is selected from clomipramine, fluvoxamine, fluoxetine, sertraline, and paroxetine, more preferably, the SRI is a SSRI selected from the group consisting of fluvoxamine, fluoxetine, sertraline and paroxetine. Generally, the average dose of the serotonin reuptake inhibitor is from the range of from about 10 to about 200, more preferably from about 10 to about 40, mg daily. Preferably the SRI is administered orally.

If long-term maintenance therapy on SRIs are desired, the individual may initially be treated with a combination of SRI and tramadol in order to obtain a rapid decrease in the OC spectrum disorder symptoms. After sufficient time has passed for the SRI response to occur, generally from about 8 to 10 weeks, the level of tramadol may be slowly tapered off until the individual is being treated only with the SRI.

Non-limiting examples of tramadol treatment for obsessive-compulsive spectrum disorders are set forth below.

EXAMPLE 1

Seven SRI-refractory patients who met the DSM-IV criteria for OCD for at least six months, who had a minimum score of 15 on the Y-BOCS, and who had SRI-treatment refractory OCD, as defined as having an inadequate response to an 8 week therapeutic dose of at least one SRI, were recruited for a clinical study. Exclusion criteria for the study included a life-time DSM-IV diagnosis of mania, psychotic disorder, alcohol or substance abuse or dependence, prior history of hypersensitivity to tramadol or any other opioid, a history of seizures, including childhood febrile seizures, and any clinically relevant abnormal laboratory results or clinically unstable medical conditions. The 7 patients had a mean duration of illness of 27.4±9.5 years, and mean previously failed SRI trials of 2.9±2.1. The patients were not concurrently receiving behavioral therapy.

Patients were evaluated using the Yale-Brown Obsessive Compulsive Scale (Y-BOCS), the Hamilton Rating Scale for Depression (HAM-D) and the Clinical Global Impression Scale (CGI). Subsequent to screening, the individuals received a six week treatment with tramadol hydrochloride. The tramadol hydrochloride was initially administered at 50 mg four times a day for the first week. If there was less than a 20% drop in baseline Y-BOCS scores by the end of week one, the tramadol hydrochloride dose was advanced slowly over 1 to 2 weeks to a maximum of 400 mg per day in 3 to 5 divided doses. Weekly measurements with the Y-BOCS, HAM-D and CGI were used to assess responses. Y-BOCS and HAM-D values at the start and end of the trial were compared using the Wilcoxon signed-ranks test. One patient elected to discontinue medication during week 1 due to nausea and exacerbation of trichotillomania, while another patient discontinued medication during week 6 after experiencing a panic attack.

The mean ± standard deviation dose of tramadol hydrochloride for the six patients completing at least two weeks was 254±119 mg/day (divided into from 3 to 5 doses). The mean ± standard deviation of baseline and endpoint Y-BOCS, HAM-D and severity of illness CGI and global improvement CGI are set forth below in Table 1. For severity of illness CGI, 4=moderately ill, 5=markedly ill, and 6=severely ill, while for global improvement CGI, 2=much improved, 3=minimally improved, 4=no change, 5=minimally worse, and 6=much worse. The scores for the patient who dropped out in week 6 were carried forward from week 5.

TABLE 1

Outcome Measurement Scores at Baseline and Endpoint Treatments for Six Patients Completing at Least Two Weeks of Tramadol Hydrochloride Treatment

| SCALE | BASELINE | ENDPOINT |
|---|---|---|
| Y-BOCS, mean ± SD | 27.8 ± 4.6 | 20.7* ± 5.7 |
| HAM-D, mean ± SD | 27.7 ± 15.9 | 28.8 ± 9.8 |
| Severity of Illness CGI, mean ± SD | 5.3 ± 1.5 | 4.5 ± 1.2 |
| Global Improvement CGI, mean ± SD | 5.2 ± 0.8 | 2.3 ± 1.0 |

*Z = 2, df = 1, P < 0.05

During tramadol hydrochloride treatment the Y-BOCS scores decreased while there was no significant change in HAM-D scores. While not being bound by theory, it is believed that tramadol hydrochloride may be effecting the symptoms of OCD in SRI treatment refractory patients via different mechanisms than inhibition of serotonin reuptake. Three of the seven patients displayed a large decrease (greater than 6 point) in their Y-BOCS scores within the first week, indicating a rapid onset of response.

Patients reported that although obsessions persisted in a muted form, the urges or pressures to perform the compulsions were diminished. The change in compulsive symptoms was particularly pronounced in the patients exhibiting a rapid response (a greater than 6 point drop in Y-BOCS scores within the first week). Two individuals reported alleviation in compulsive urges after the first 50 mg dose of tramadol hydrochloride.

The patients reported decreased appetite, and on average lost 5.86 pounds. Weekly mean ± standard deviation of weight and tramadol doses for the patients are set forth below in Table 2, while weights and tramadol hydrochloride doses for individual patients are set forth in Table 3. For data analysis purposes, when an individual's weight was not available, the weight from the previous week was carried forward.

TABLE 2

Weight and Tramadol Hydrochloride Dose for Seven Patients

| Visit | Weight, mean ± SD (lbs) | Tramadol Hydrochloride, mean ± SD (mg/day) |
| --- | --- | --- |
| Baseline | 173.36 ± 29.58 | 0 ± 0 |
| Week 1 | 172.46 ± 29.9 | 157.14 ± 60.75 |
| Week 2 | 170.39 ± 29.1 | 221.43 ± 118.52 |
| Week 3 | 170.5 ± 29.64 | 242.86 ± 97.59 |
| Week 4 | 169.46 ± 28.62 | 257.14 ± 83.8 |
| Week 5 | 169.1 ± 28 | 264.29 ± 98.8 |
| Week 6 | 167.5 ± 26.54 | 253.57 ± 115.86 |

TABLE 3

Effect of Tramadol on Weight of Individual Patients

| Patient | Visit | Weight (lbs) | Tramadol Hydrochloride (total mg/day) |
| --- | --- | --- | --- |
| 1 | Baseline | 129.5 | 0 |
|   | Week 1 | Not Available | 200 |
|   | Week 2 | 128.25 | 300 |
|   | Week 3 | 127 | 400 |
|   | Week 4 | 127.25 | 400 |
|   | Week 5 | Not Available | 400 |
|   | Week 6 | 126 | 300 |
|   | Week 7 | 126.3 | 300 |
|   | Week 8 | 126 | 300 |
| 2 | Baseline | 178 | 0 |
|   | Week 1 | 182 | 200 |
|   | Week 2 | 179 | 400 |
|   | Week 3 | 180 | 300 |
|   | Week 4 | 180 | 300 |
|   | Week 5 | 180 | 300 |
|   | Week 6 | 181 | 350 |
|   | Week 7 | 179 | 350 |
| 3* | Baseline | 149 | 0 |
|   | Week 1 | 142.5 | 200 |
| 4 | Baseline | 207 | 0 |
|   | Week 1 | 202.25 | 200 |
|   | Week 2 | 200 | 300 |
|   | Week 3 | 200 | 300 |
|   | Week 4 | 196 | 300 |
|   | Week 5 | Not Available | 350 |
|   | Week 6 | 190 | 400 |
| 5 | Baseline | 156 | 0 |
|   | Week 1 | Not Available | 50 |
|   | Week 2 | 154 | 50 |
|   | Week 3 | Not Available | 100 |
|   | Week 4 | 153.5 | 150 |
|   | Week 5 | 154 | 150 |
| 6 | Baseline | 206 | 0 |
|   | Week 1 | 205 | 150 |
|   | Week 2 | 203 | 150 |
|   | Week 3 | 204 | 200 |
|   | Week 4 | 203 | 250 |
|   | Week 5 | 200 | 300 |
|   | Week 6 | 194 | 300 |
| 7 | Baseline | 188 | 0 |
|   | Week 1 | 190 | 100 |
|   | Week 2 | 186 | 150 |
|   | Week 3 | 186 | 200 |
|   | Week 4 | Not Available | 200 |
|   | Week 5 | 184 | 150 |
|   | Week 6 | 185 | 75 |

*Patient dropped out of study due to nausea and exacerbation of trichotillomania At the end of six weeks, 3 patients chose to continue on tramadol hydrochloride, one chose to discontinue tramadol hydrochloride and switch to another pharmacologic agent, and three (including the individuals who dropped out of the study early) discontinued tramadol hydrochloride without starting another agent. Tramadol hydrochloride withdrawal Y-BOCS scores were followed for two weeks for the 3 patients stopping tramadol hydrochloride without adding another pharmacological agent, and were found to increase from an average of 14.3 to 19.7.

EXAMPLE 2

A 27 year old female with a ten year history of OCD showed a worsening of symptoms after the birth of her child. Prior to tramadol hydrochloride treatment the patient had a Y-BOCS score of 26. Within 24 hours of being placed on a tramadol hydrochloride treatment of 50 mg twice a day, the patient reported a decrease in obsessions and compulsions. Thus, the patient showed a rapid therapeutic response to the tramadol hydrochloride within the first 24 hours.

After one week of tramadol hydrochloride treatment the patient's Y-BOCS score had decreased to 19. The tramadol hydrochloride therapy was then supplemented with 20 mg per day of fluoxetine, and three weeks later the fluoxetine was increased to 40 mg daily. During the first month of treatment, the patient required up to 350 mg of tramadol hydrochloride daily in divided doses as needed to diminish her OCD symptoms (generally from 50 to 100 mg 4 times a day). The dose of tramadol hydrochloride was increased by approximately 50 to 100 mg weekly over the first three weeks due to the tolerance to anti-obsessive effects. Six weeks after the initiation of the combination of tramadol hydrochloride and fluoxetine, the patient's Y-BOCS scores had decreased to 10, and the patient found she no longer required the tramadol hydrochloride.

EXAMPLE 3

A female OCD patient was treated with tramadol hydrochloride for a total of 11 months, during the last month of the study the patient was titrated off the tramadol hydrochloride. The only additional prescribed medication was alendronic acid ((4-amino-1-hydroxybutylidene)bisphosphonic acid) started at week 6 for osteoporosis unrelated to tramadol use. (The patient has a family history of osteoporosis and previous steroid use.) The patient's weight and tramadol hydrochloride doses are set forth in Table 4 below.

TABLE 4

Effect of Tramadol Hydrochloride on Weight

| Visit | Weight (lbs) | Tramadol Hydrochloride (total mg/day) |
|---|---|---|
| Baseline | 129.5 | 0 |
| Week 1 | Not Available | 200 |
| Week 2 | 128.25 | 300 |
| Week 3 | 127.0 | 400 |
| Week 4 | 127.25 | 400 |
| Week 5 | Not Available | 400 |
| Week 6 | 126.0 | 300 |
| Week 7 | 126.3 | 300 |
| Week 8 | 126.0 | 300 |
| Month 3 | 127.0 | 350 mg/day for 2 weeks, followed by 400 mg/day |
| Month 4 | 124.5 | 400 |
| Month 5 | 124.75 | 400 |
| Month 6* | 124.5 | 400 |
| Month 7 | 127.0 | 400 |
| Month 8 | 125.0 | 400 |
| Month 9 | 128.0 | 300 |
| Month 10 | 127.5 | 150 |
| Month 11 | 131.5 | 100 mg/day for 2 weeks, followed by 50 mg/day for 1 week, then discontinued |

*Alendronic acid started

As indicated by the data in Table 4, the patient lost weight during the tramadol hydrochloride treatment, however, the weight was regained after the tramadol hydrochloride treatment was discontinued.

EXAMPLE 4

A 45 year old male patient with a history of recurrent major depressant disorder was treated with extended release bupropion (1-(3-chlorophenyl)-2-[(1,1-dimethylethyl) amino]-1-propane), at a total dose of 300 mg per day (200 mg in the morning and 100 mg in the evening). The patient had a long history of motor and vocal tics, and the motor tics were found to worsen while patient was taking bupropion. The patient also reported a history of purging. The patient exhibited no suicidal ideation or homicidal ideation, and exhibited no manic symptoms while on the bupropion. It was determined the patient did not suffer from bipolar affective disorder or psychosis. The patient was diagnosed as having major depressant disorder and Tourette's syndrome.

The bupropion was supplemented with 50 mg twice a day of tramadol. After about two weeks the patient reported no major change in level of depression, suggesting tramadol itself has no immediate effect on depression. However, the patient did report that taking 50 mg tramadol twice a day reduced the number of motor tics without any side effects. The patient estimated that the number of tics was reduced by about two-thirds after starting the tramadol. The patient's bupropion dose was increased to 400 mg per day (200 mg twice a day), while the tramadol dose was maintained at 50 mg twice a day. The patient was informed the tramadol dose could be increased to 50 mg four times a day if the number of tics increased.

Additional embodiments and modifications within the scope of the claimed invention will be apparent to one of ordinary skill in the art. Accordingly, the scope of the present invention shall be considered in terms of the following claims, and is understood not to be limited to the details of the methods and examples described in this specification.

What is claimed is:

1. A method of treating an obsessive-compulsive spectrum disorder, comprising the step of administering an effective amount of tramadol to an individual in need thereof.

2. A method according to claim 1, wherein the tramadol is in the form of a hydrochloride salt.

3. A method according to claim 1, wherein the obsessive-compulsive spectrum disorder is selected from the group consisting of obsessive-compulsive disorder, Tourette's syndrome, body dismorphic disorder, hypochondriasis, eating disorders, impulse control disorders, paraphilias and nonparaphilic sexual addictions, Sydeham's chorea, torticollis, autism and combinations thereof.

4. A method according to claim 3, wherein the obsessive-compulsive spectrum disorder is an impulse control disorder selected from the group consisting of intermittent explosive disorder, kleptomania, pathological gambling, pyromania, compulsive shopping, compulsive buying, repetitive self-mutilation, onychophagia, psychogenic excoriation, trichotillomania and combinations thereof.

5. A method according to claim 2, wherein the obsessive-compulsive spectrum disorder is obsessive-compulsive disorder.

6. A method according to claim 1, wherein the individual is refractory to serotonin reuptake inhibitors.

7. A method according to claim 2, comprising the step of administering from about 50 to about 400 mg of tramadol hydrochloride per day to an individual.

8. A method according to claim 7, wherein the total daily amount of tramadol hydrochloride is administered in from about 2 to about 5 doses.

9. A method according to claim 1, wherein the individual exhibits a decrease in Yale-Brown Obsessive-Compulsive Scale score after about fourteen days of treatment.

10. A method according to claim 1, further comprising the step of administering a serotonin reuptake inhibitor to the individual.

11. A method according to claim 10, wherein the serotonin reuptake inhibitor is selected from the group consisting of clomipramine, fluoxetine, fluvoxamine, sertraline, paroxetine and mixtures thereof.

12. A method according to claim 1, wherein the tramadol is administered by a transepidermal patch.

13. A method of obtaining a treatment response to an obsessive-compulsive spectrum disorder in less than fourteen days, comprising the step of administering an effective amount of tramadol to an individual in need thereof.

14. A method according to claim 13, wherein the tramadol is in the form of a hydrochloride salt.

15. A method according to claim 13, wherein the individual exhibits a decrease in Yale-Brown Obsessive-Compulsive Scale score after about fourteen days of treatment.

16. A method according to claim 13, wherein the individual exhibits a decrease in Yale-Brown Obsessive-Compulsive Scale score after about seven days of treatment.

17. A method according to claim 13, further comprising treating the individual with behavior modification therapy.

18. A method according to claim 14, comprising the step of administering from about 50 to about 400 mg of tramadol hydrochloride per day to the individual.

19. A method according to claim 18, wherein the total daily amount of tramadol hydrochloride is administered in from about 2 to about 5 doses.

20. A method according to claim 13, further comprising the step of administering a serotonin reuptake inhibitor to the individual.

21. A method according to claim 20, wherein the serotonin reuptake inhibitor is selected from the group consisting of clomipramine, fluoxetine, fluvoxamine, sertraline, paroxetine and mixtures thereof.

22. A method according to claim 20, comprising orally administering from about 10 to about 200 mg of a serotonin reuptake inhibitor per day to the individual.

23. A method according to claim 13, wherein the obsessive-compulsive spectrum disorder is selected from bulimia nervosa and binge eating disorder, and further wherein the individual has a decreased appetite after about 14 days of treatment.

24. A method of treating an obsessive-compulsive spectrum disorder, comprising the step of administering an effective amount of tramadol to and individual in need thereof on an as-needed basis.

25. A method according to claim 24, wherein the obsessive-compulsive spectrum disorder is Tourette's syndrome.

26. A method according to claim 25, wherein the tramadol is in the form of a hydrochloride salt.

27. A method according to claim 26, wherein the step of administering tramadol hydrochloride comprises orally administering from about 50 to about 200 mg tramadol hydrochloride.

28. A method according to claim 27, wherein the step of administering tramadol hydrochloride comprises orally administering the tramadol hydrochloride at least about one hour prior to the point in time at which a decrease in Tourette's syndrome symptoms is desired.

* * * * *

UNITED STATES PATENT AND TRADEMARK OFFICE
CERTIFICATE OF CORRECTION

PATENT NO.    : 6,387,956 B1
DATED         : May 14, 2002
INVENTOR(S)   : Nathan A. Shapira et al.

It is certified that error appears in the above-identified patent and that said Letters Patent is hereby corrected as shown below:

Column 14,
Line 1, change "and" to -- an --.
Line 12, change "claim 27" to -- claim 26 --.

Signed and Sealed this

Thirteenth Day of August, 2002

Attest:

Attesting Officer

JAMES E. ROGAN
Director of the United States Patent and Trademark Office

UNITED STATES PATENT AND TRADEMARK OFFICE
CERTIFICATE OF CORRECTION

PATENT NO.     : 6,387,956 B1
DATED          : May 14, 2002
INVENTOR(S)    : Shapira et al.

It is certified that error appears in the above-identified patent and that said Letters Patent is hereby corrected as shown below:

Title page,
Item [56], OTHER PUBLICATIONS, Mc Conville et al reference, change "sequential use of oploid antagoinists" to -- sequential use of oploid antagonists --.

Column 2,
Line 42, change "intermitted" to -- intermittent --.
Line 47, change "experience increasing" to -- experience an increasing --.

Column 3,
Line 13, change "such a bulimia" to -- such as bulimia --.
Line 22, change "intermitted" to -- intermittent --.
Line 30, change "*Clim.*" to -- *Clin.* --.
Line 41, change "Thus there is" to -- Thus, there is --.

Column 11,
Line 44, change "while patient" to -- while the patient --.

Signed and Sealed this

Tenth Day of December, 2002

JAMES E. ROGAN
*Director of the United States Patent and Trademark Office*